United States Patent [19]

Durbak et al.

[11] 4,241,048
[45] Dec. 23, 1980

[54] SUSPENSION COMPOSITION OF BENZOCAINE

[75] Inventors: Taras Durbak, Irvington; Ara Nersesian, Livingston, both of N.J.

[73] Assignee: Bristol-Myers Company, New York, N.Y.

[21] Appl. No.: 35,115

[22] Filed: May 1, 1979

[51] Int. Cl.³ .......................... A61K 31/79; A61L 9/14
[52] U.S. Cl. .......................................... 424/45; 424/78; 424/80; 526/264
[58] Field of Search .................... 526/264; 424/45, 78, 424/80

[56] References Cited

U.S. PATENT DOCUMENTS

| 2,045,125 | 6/1936 | Curtis | 424/60 |
|---|---|---|---|
| 2,187,597 | 1/1940 | Blaso | 424/60 |
| 2,187,598 | 1/1940 | Blaso | 424/60 |
| 2,286,718 | 6/1942 | Curtis | 424/317 |
| 2,628,182 | 2/1953 | Reasenberg | 424/60 |
| 2,801,201 | 7/1957 | Kipnis | 424/60 |
| 3,019,163 | 6/1962 | Harnist | 424/60 |
| 3,145,194 | 8/1964 | Heckmaier et al. | 526/264 |
| 3,166,525 | 1/1965 | Perry | 526/264 X |
| 3,287,272 | 11/1966 | Katzenstein | 526/264 X |
| 3,294,765 | 12/1966 | Hart et al. | 526/264 |
| 3,322,624 | 5/1967 | Stone | 424/47 |
| 3,330,885 | 7/1967 | Dalton et al. | 252/316 |
| 3,427,296 | 2/1969 | Anspon et al. | 526/264 |
| 3,437,647 | 4/1969 | Freifeld | 526/264 X |
| 3,577,516 | 5/1971 | Gould et al. | 424/47 |
| 3,730,960 | 5/1973 | Watchung et al. | 424/78 |
| 3,770,648 | 11/1973 | Mackles | 252/305 |
| 3,872,023 | 3/1975 | Baum et al. | 252/316 |
| 3,896,033 | 7/1975 | Grimm | 258/8.8 |
| 3,909,444 | 9/1975 | Anderson et al. | 252/316 |
| 3,914,283 | 10/1975 | Okamoto et al. | 260/472 |
| 3,943,063 | 3/1976 | Morishita et al. | 252/316 |
| 3,957,966 | 5/1976 | Valan | 424/33 |
| 4,053,696 | 10/1977 | Herrle et al. | 526/264 X |

FOREIGN PATENT DOCUMENTS

| 730449 | 5/1955 | United Kingdom | 526/264 |
|---|---|---|---|
| 828970 | 2/1960 | United Kingdom | 526/264 |
| 1088109 | 10/1967 | United Kingdom | 526/264 |
| 1421529 | 1/1976 | United Kingdom | 526/264 |
| 174355 | 1/1966 | U.S.S.R. | 526/264 |

Primary Examiner—Dale R. Ore
Attorney, Agent, or Firm—Irving Holtzman; George A. Mentis

[57] ABSTRACT

A composition containing a therapeutically effective amount of powdered benzocaine suspended in an essentially anhydrous carrier and further containing a copolymer of a vinylpyrrolidone and an alpha-olefin as a crystal growth suppressing agent.

19 Claims, 1 Drawing Figure

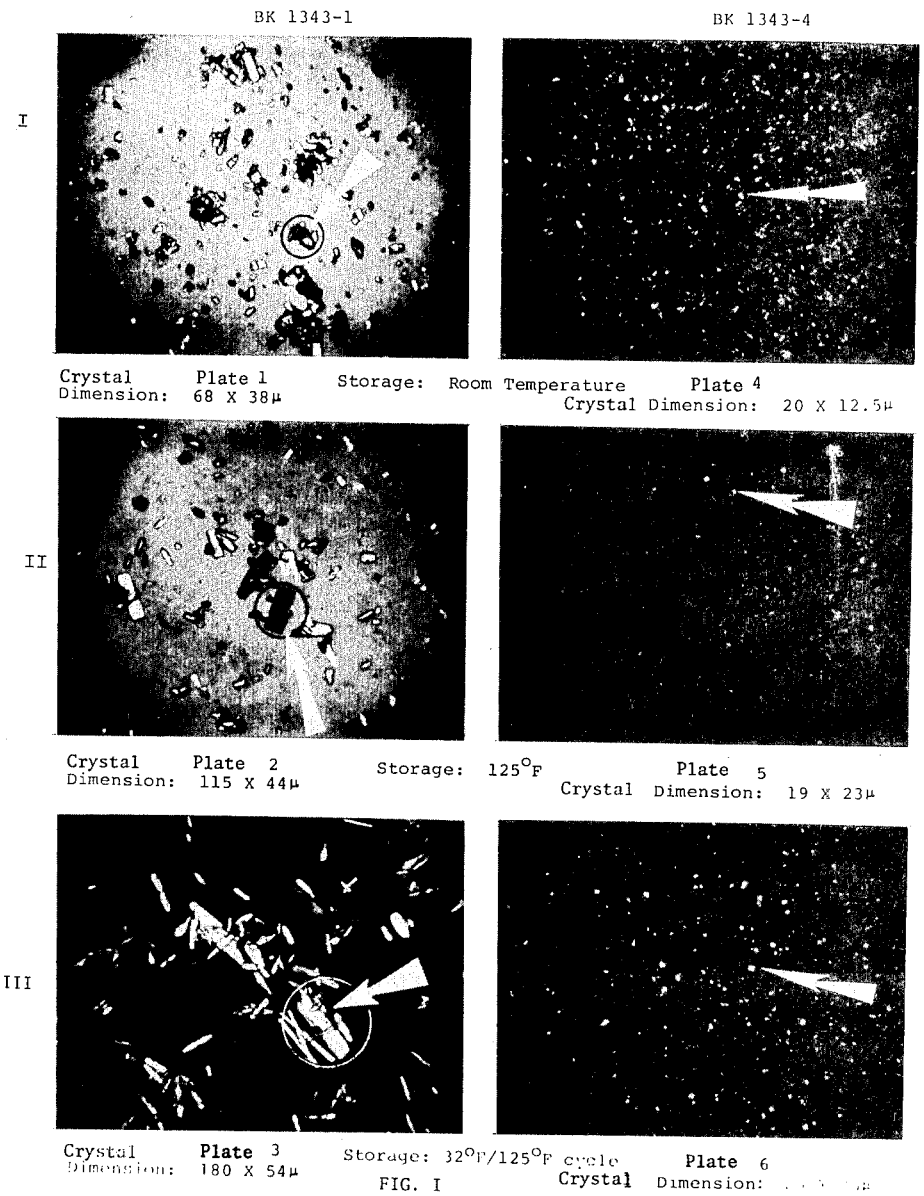
FIG. I

SUSPENSION COMPOSITION OF BENZOCAINE

This invention relates to compositions containing benzocaine and, more particularly, to compositions of this character in which benzocaine powder is present as a suspension in a vehicle that is essentially anhydrous.

Benzocaine is a well-known topical anesthetic and is widely used because of this property in a variety of pharmaceutical preparations. In many of its uses, it has been found convenient or efficacious to suspend the powdered benzocaine in an anhydrous vehicle. In the typical preparation, benzocaine in finely powdered form is incorporated as a suspension of a vehicle in which it has at most limited solubility.

It has been found, however, that when products of this character are stored over a period of time, and particularly stored at fluctuating temperatures, the benzocaine which previously existed in powdered form, changes its form becoming large, sharp needlelike crystals. This behavior of benzocaine is believed to be due to the fact that it has poor temperature dependent solubility in the vehicles in which it is suspended e.g. oils and fats. At elevated temperatures, a part of the benzocaine will dissolve in the oil and, upon cooling, the benzocaine will crystallize out as large needles. On repeated warming/cooling cycles, the amount of benzocaine powder will decrease and the needle crystalline form will increase until practically all the fine powder is converted into large, needlelike crystals.

This represents a decided drawback since this crystal growth gives the product containing the benzocaine a gritty feel limiting its usefulness in the treatment of some conditions e.g. hemorrhoids. In addition, when the benzocaine preparation is packaged in a pressurized aerosol container, the crystal growth of the benzocaine tends to produce a high incidence of valve clogging.

It has now been found that this undesired crystal growth in benzocaine suspension products can be prevented by incorporating in said compositions an effective amount of linear copolymer of a vinylpyrrolidone and a long chain alpha-olefin.

It is accordingly an object of the present invention to provide a powdered benzocaine type suspension product in which the tendency for crystal growth of benzocaine on storage, and particularly storage at fluctuating temperatures is substantially reduced or minimized.

It is also an object of the present invention to provide a product of the aforesaid type which contains therein as a benzocaine crystal-forming-suppressing agent a linear copolymer of a vinylpyrrolidone and a long chain alpha-olefin.

Other and more detailed objects will be apparent from the following description and claims.

FIG. 1 is photomicrographs of samples of the various products after storage under the conditions specified; the dimensions of the marked crystals being indicated below Plate.

The linear copolymers of a vinylpyrrolidone and a long chain alpha-olefin that can be employed in the present invention can be described by the following formula:

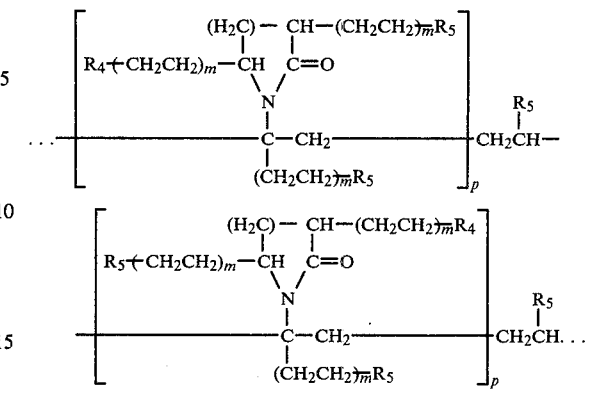

wherein $R_5$ is selected from the group consisting of hydrogen and alkyl, of from 1 to about 180 carbon atoms, p is an integer of from 10 to 100, and wherein the m's independently represent a numerical value of 0 to 1; when m is zero, $R_5$ is hydrogen; when m is 1, $R_5$ is selected from the group consisting of hydrogen and alkyl of from 1 to about 180 carbon atoms, and wherein at least one of the m's in at least one of the N-vinyl pyrrolidone moieties has the value of 1.

The vinylpyrrolidone-long chain alpha-olefin copolymers that may be employed herein have a wide range of molecular weights (about 7,000 to about 20,000) with various long chain alkyls and with various ratios of long chain allylation. In physical appearance, they range from liquids to solids. Their solubility characteristics range from mineral oil soluble to water dispersible.

Typical of the vinylpyrrolidone-long chain alpha-olefin copolymers that are useful for the present purposes are manufactured by the GAF Corporation under the trade name of Ganex V polymers. At the present time, two grades of Ganex V polymers are commercially available: (1) V-216 is a liquid material soluble in oils and/or solvents. It contains $C_{16}$ alkyls at about 80% substitution ratio and has an average molecular weight of 7,300. The CTFA adopted name is PVP-Hexadecene Copolymer; (2) V-220 is a waxy solid with a melting point of 32°–36° C. and is soluble in oils and solvents. It contains $C_{20}$ alkyls at about 70% substitution ratio and has an average molecular weight of 8,600. The CTFA adopted name is PVP-Eicosene Copolymer (See GAF Corporation Ganex V Polymer Bulletin 1977 and GAF Corporation Ganex V Polymer Preliminary Data Sheet 752–65 including Toxicity Data which are incorporated herein by way of reference).

The quantity of the vinylpyrrolidone-long chain alpha-olefin copolymer that will be incorporated in the products of the present invention will, for the most part, depend upon the amount of benzocaine they contain. To achieve crystal growth inhibition, in accordance with this invention, generally the ratio of vinylpyrrolidone long chain alpha-olefin copolymer to benzocaine employed should be in the range of from about 0.05 to 4 parts of copolymer (and preferably 0.2 to 1 part of copolymer) and 1 part of benzocaine.

The quantity of benzocaine that may be included in the present compositions is not particularly critical. They should of course contain enough to be therapeutically effective. Ordinarily, the benzocaine concentration will fall in the range of 1% to 30% by weight and preferably 2% to 20% by weight based on the total weight of the composition. The upper level, however, is not limited and it may be as high as the product can tolerate.

The essentially anhydrous vehicles for the benzocaine and copolymer that can be employed in the present invention can take a variety of forms. Thus, for example, it might take the form of an organic liquid in which the benzocaine and copolymer are suspended. The quantity of these liquid vehicles in the compositions of this invention may vary somewhat. Ordinarily, however, it will usually constitute from 40.0% to 95% by weight of the total composition.

The types of liquid vehicles that can be used are also quite varied and the particular liquid selected is of no great critical significance. Typical among the organic liquids which are useful, alone or in combination, include: hydrocarbon oils e.g. mineral oil, petroleum oils, liquid petrolatums; petroleum solvents; fatty acid esters e.g. isopropyl myristate, isopropyl palmitate, butyl stearate, glycol dioleate, dioctyl sebacate, etc.; vegetable oils e.g. coconut oil, peanut oil, soybean oil, linseed oil, etc.; fatty acids e.g. coconut fatty acid, oleic acid, isostearic acid, lauric acid, etc.; fatty alcohols e.g. lauryl alcohol, oleyl alcohol, hexadecyl alcohol, etc.; mixtures of organic liquids e.g. chlorinated hydrocarbons and mineral oil, methyl salicylate, homo menthyl salicylate, etc.; dimethyl silicone fluids (nonvolatile and volatile) and their derivatives.

The liquid vehicles can be modified by the inclusion of liquid or solid additives in order to change their solubility, viscosity or organoleptic characteristics. The liquid additives can be selected from the group of polyalkylene glycols and their derivatives such as Ucon fluids: Ucon LB, Ucon 50HB, Ucon 75H [these are reaction products of butyl alcohol and propylene oxide, butyl alcohol and propylene oxide and ethylene oxide (50%/50%), and butyl alcohol and propylene oxide (25%) and ethylene oxide (75%)]; polyalkylene block copolymers of the Poloxamer or Meroxapol type; polyalkylene triols, etc. These additives are good benzocaine solvents but when used in combination with the basic carriers do not dissolve benzocaine and retain it in the suspended form.

The solid additives for inclusion in the liquid carrier include solid waxes, fats or other solid materials, typical of which are petroleum gellies and waxes; cocoa butter; natural and synthetic alkyl glycerides; glycol and polyol alkyl esters or ethers; natural waxes of plant, animal or insect origin and/or their synthetic substitutes; polyethylene wax polymers and copolymers; other similar suitable substances.

The quantity of said liquid or solid additives that may be employed in the composition of this invention that employ a liquid vehicle will vary depending upon the result that is desired. Ordinarily, when they are employed, they will constitute between about 1% to about 40% by weight based on the total weight of the composition.

Another component that is advantageously used in the liquid vehicle compositions of this invention is a suitable suspending agent. Typical among the suspending agents which are known in the art and are useful for the present purposes include: quaternium 18 hectorite, quaternium 18 bentonite and stearalkonium hectorite; polyethylene based homo polymers and copolymers; micronized and fumed silicas, glyceryl hydroxystearates; aluminum stearates; etc. The clay type suspending agents require a suitable polar agent such as ethanol, propylene carbonate or a surfactant to promote the gelling.

The quantity of suspending agent utilized may vary somewhat. Usually, however, this will constitute between about 0.25% to about 10% by weight and preferably between about 0.5% to about 4% by weight based on the total weight of the composition.

Liquid vehicle compositions of this invention can be dispensed as sprays or foams by packaging them in suitable spray pump or aerosol containers. When a foam is chosen, the inclusion of an appropriate foaming agent is desirable. The formulations dispensed from aerosol containers will contain compatible propellants.

Typical foaming agents useful for the compositions of this invention include resinous silicone copolymers which have been described in detail in the U.S. Patent to Leonard Mackles U.S. Pat. No. 3,770,648. Also, the suitable propellant systems have been described in the above cited patent.

The essentially anhydrous carrier of the present invention may also be a solid. In this case, the composition may take the form of an ointment, suppository, anhydrous cream, gel, etc. A typical carrier for an ointment is petrolatum; whereas, for a suppository type composition, a typical carrier would be cocoa butter or its substitute. However, it is within the scope of this invention to use any anhydrous cream, ointment, gel or suppository base known in this art as suspension carriers. The quantity of solid carrier that can be employed will obviously vary widely. Ordinarily, this will constitute between about 40% to 95% by weight based on the total weight of the composition.

As in the case with the liquid vehicle, it is sometimes useful to use a suspending agent when the solid vehicle is employed. In this case, the suspending agent will comprise from about 0.25% to about 10% by weight and preferably from about 0.5% to about 4% by weight based on the total weight of the composition.

The above said compositions can also contain additional adjuncts known in the art to obtain special required properties. This may be the case where the carrier is a liquid or a solid. By way of example, the following may be mentioned:

1. Surfactants to impart rinsing, spreading and cleansing properties such as polyol esters and diesters, sorbitan esters, polyalkylene sorbitan esters, phosphate esters, polyol ethers, lecithins, alkanolamides, etc.

2. Protectants such as zinc oxide, alumina gel, cocoa butter, lanolin and its derivatives, petrolatum, shark liver oil, bismuth subnitrate, etc.

3. Vasoconstrictors such as ephedrine and its salts, phenylephrine and its salts, epinephrine, etc.

4. Anti-inflammatory agents such as derivatives of the corticosteroids, hydrocortisone alcohol or hydrocortisone acetate, etc.

5. Counterirritants such as camphor, menthol, resorcinol, eucalyptus oil, etc.

6. Additional local anesthetics such as benzyl alcohol, diperodon hydrochloride, pramoxine hydrochloride, etc.

7. Opacifiers such as titanium dioxide, zinc oxide, etc.

8. Antioxidants such as butylated hydroxyanisole, butylated hydroxytoluene, alpha-tocopherol and its derivatives, ascorbic acid and its derivatives, dialkylthiodipropionates, etc.

9. Preservatives, perfumes and colors.

10. Other additives such as retinol (Vitamin A) and its derivatives; collagen, soluble or microcrystalline; proteins and their hydrolysates; antihistamines such as chlorpheniramine maleate, diphenhydramine hydrochloride, etc.

This invention can be applied to any anhydrous preparation containing benzocaine as a local anesthetic. In addition to hemorrhoidal products, it can also be applied to burns, sunburn, poison ivy, insect bite, otic (ear), teething (gums) preparations, etc.

The following Examples are given to further illustrate this invention. It is to be understood, however, that the invention is not limited thereto.

The terms used in the Examples and elsewhere in this application are generally the CTFA designated names listed in the CTFA Cosmetic Ingredient Dictionary, Second Edition (1977). However, materials which are listed in the CTFA Dictionary as a group, or which are not listed in the CTFA Dictionary, are given below:

Cab-O-Sil M-5: Fumed silicon dioxide, 0.012 micron particle size, manufactured by the Cabot Corporation, Boston, Mass.

A-C Polyethylene 617: Ethylene homopolymer, softening point of 102° C., hardness 8.0 dmm, density 0.91 g/cc, viscosity at 140° C. 180 cps, manufactured by Allied Chemical Corp., Specialty Chemicals Division.

Thixcin R: Trihydroxystearin, glyceryl tri(12-hydroxystearate), a suspending agent manufactured by the NL Industries, Hightstown, New Jersey.

Silicone CS-4262: 50% solution in isopropyl myristate of resin containing $SiO_2$ units and $(CH_3)_3SiO_{\frac{1}{2}}$ units in which the ratio of $SiO_2$ units to $(CH_3)_3SiO_{\frac{1}{2}}$ units is 1.33 (or 0.75 to 0.25) having an average M.W. of 5000 to 8000; hydroxy content of 3 to 5% by weight based on the total weight resin and a viscosity (50% xylene solution) of 4 to 8 centistokes at 25° C., manufactured by General Electric, Silicone Products Department.

Siloxane F-251: A volatile silicone consisting of a mixture of low molecular weight cyclic dimethylpolysiloxanes (cyclomethicones) with specific gravity 0.95, viscosity at 25° C. of 3.1 cs, flash point 80° C., boiling point 182° C., manufactured by the SWS Silicones Corp., Adrian, Michigan.

Wecobee M: A synthetic triglyceride derived from coconut and palm kernel oils, saponification value 243, melting point 96/80° F., viscosity at 150° F., 13.5 cp, manufactured by the PVO International Inc.

| Liquid Suspensions | Ex. 1 | Ex. 2 | Ex. 3 | Ex. 4 | Ex. 5 | Ex. 6 |
|---|---|---|---|---|---|---|
| Quaternium 18 Hectorite | 1.0 | 2.0 | — | — | — | 1.0 |
| Cab-O-Sil M-5 | — | — | 2.0 | — | — | — |
| A-C Polyethylene 617 | — | — | — | 4.0 | — | — |
| Thixcin R | — | — | — | — | 3.5 | — |
| PEG 8 Dilaurate | 2.0 | 2.0 | 2.0 | 2.0 | — | 2.0 |
| Benzocaine | 5.0 | 5.0 | 5.0 | 5.0 | 2.0 | 5.0 |
| PVP Eicosene Copolymer | 2.0 | 1.0 | 1.0 | 2.0 | 2.0 | 2.0 |
| Mineral Oil 80/90 SSU | 90.0 | 83.95 | 83.9 | 87.0 | 87.2 | 88.85 |
| Cocoa Butter | — | 5.0 | 5.0 | — | — | — |
| Zinc Oxide | — | — | — | — | 5.0 | — |
| Phenylephrine Palmitate | — | — | — | — | — | 0.1 |
| Butylated Hydroxytoluene | — | 0.05 | — | — | — | 0.05 |
| Silicone CS-4262 | — | 1.0 | 1.0 | — | — | 1.0 |
| Perfume | — | — | 0.1 | — | 0.3 | — |
| | 100.0 | 100.0 | 100.0 | 100.0 | 100.0 | 100.0 |

| Aerosolized Foams | Ex. 7 | Ex. 8 | Ex. 9 | Ex. 10 | Ex. 11 | Ex. 12 | Ex. 13 |
|---|---|---|---|---|---|---|---|
| Quaternium 18 Hectorite | 0.94 | 0.94 | 0.94 | 0.94 | 0.94 | 1.88 | 0.94 |
| PEG 8 Dilaurate | 1.88 | 1.88 | 1.88 | 1.88 | 1.88 | 1.88 | 1.88 |
| Benzocaine | 4.70 | 4.70 | 4.70 | 4.70 | 4.70 | 14.10 | 1.88 |
| PVP Eicosene Copolymer | 0.94 | 0.94 | — | 4.70 | 1.88 | 9.40 | 0.94 |
| PVP Hexadecene Copolymer | — | — | 1.88 | — | — | — | — |
| Mineral Oil 80/90 SSU | 79.76 | 79.29 | 78.91 | 79.76 | 38.82 | 60.02 | 42.58 |
| Cocoa butter | 4.70 | 4.70 | 4.70 | — | 4.70 | 4.70 | 4.70 |
| Siloxane F-251 | — | — | — | — | 40.00 | — | 40.00 |
| Hydroxycortisone acetate | — | 0.47 | — | — | — | — | — |
| Butylated hydroxy toluene | 0.05 | 0.05 | 0.05 | 0.05 | 0.05 | 0.05 | 0.05 |
| Silicone CS 4262 | 0.94 | 0.94 | 0.94 | 1.88 | 0.94 | 1.88 | 0.94 |
| Perfume | 0.09 | 0.09 | — | 0.09 | 0.09 | 0.09 | 0.09 |
| Propane | 6.00 | 6.00 | 6.00 | 6.00 | 6.00 | 6.00 | 6.00 |
| | 100.00 | 100.00 | 100.00 | 100.00 | 100.00 | 100.00 | 100.00 |

| Ointments | Ex. 14 | Ex. 15 |
|---|---|---|
| Petrolatum, white | 74.75 | 72.50 |
| Lanolin, anhydrous | 5.00 | 5.00 |
| Benzocaine | 15.00 | 10.00 |
| PVP-Eicosene Copolymer | 3.00 | 5.00 |
| Camphor | 2.00 | 2.25 |
| Eucalyptus Oil | 0.25 | 0.25 |
| Zinc Oxide | — | 5.00 |
| | 100.00 | 100.00 |

| Suppositories | Ex. 16 | Ex. 17 |
|---|---|---|
| Cocoa Butter | 75.00 | — |
| Wecobee M | — | 72.5 |
| Benzocaine | 15.00 | 10.00 |
| PVP-Eicosene Copolymer | 5.00 | 15.0 |
| Zinc Oxide | 5.00 | — |
| Camphor | — | 2.25 |
| Eucalyptus Oil | — | 0.25 |
| | 100.00 | 100.00 |

To test the capability of the linear vinylpyrrolidone-long chain alpha-olefin copolymers described above to suppress benzocaine crystal growth in essentially anhydrous carriers, the following experiments were carried out.

Samples of two compositions were prepared identified as BK 1343-1 and BK 1343-4 having the formulas set forth below:

| BK 1343-1 | |
|---|---|
| | % by Wt. |
| Benzocaine | 5.00 |
| Cocoa butter | 5.00 |
| Mineral Oil 80/90 SSU | 86.00 |
| Quaternium 18 Hectorite | 1.00 |
| PEG 8 Dilaurate | 2.00 |
| Silicone CS-4262 | 1.00 |
| | 100.00 |

| BK-1343-4 | |
|---|---|
| | % by Wt. |
| Benzocaine | 5.00 |
| Cocoa butter | 5.00 |
| PVP-Eicosene Copolymer | 1.00 |
| Mineral Oil 80/90 SSU | 83.95 |
| Quaternium 18 Hectorite | 2.00 |
| PEG 8 Dilaurate | 2.00 |
| Butylated Hydroxytoluene | 0.05 |
| Silicone CS-4262 | 1.00 |
| | 100.00 |

Samples of the aforesaid compositions were stored under the following conditions:

I. Room temperature for 3 months.
II. 125° F. for 3 months.
III. 3 Months at 32°/125° F. cycles i.e. stored for at least 24 hours at each of the following temperatures respectively: room temperature, 32° F., room temperature, 105° F., 125° F., 105° F. and room temperature.

Microscopic Study

Microphotographs were made of samples of Products BK 1343-1 and BK 1343-4 after storage under the conditions described in I, II and III above. These are shown in FIG. 1 of the drawings; the dimensions of the crystals being indicated below each Plate. Product BK 1343-1 (that does not contain the vinylpyrrolidone copolymer) shows a significant growth of benzocaine crystals at room temperature; the growth being further enhanced at 125° F. and 32°/125° F. cycle storage. (See Plates 1, 2 and 3 that show clearly the crystal growth and dimensions of the largest crystal in the field). In contrast, product BK 1343-4 (containing the vinylpyrrolidone copolymer) shows very small benzocaine crystals at room temperature, 125° F. and 32°/125° F. cycle storage. In this connection, see Plates 4, 5, and 6.

Valve Clogging Study

To evaluate the valve clogging and malfunction characteristics of aerosolized benzocaine suspensions, the following tests were run. The benzocaine suspension formulations were packaged in pressurized aerosol containers and subjected to elevated temperature storage as described above. After storage at constant elevated temperatures, the aerosol cans were transferred to room temperature and then actuated once daily until the cans were evacuated completely. The cans exposed to fluctuating temperature cycles were also actuated when brought to room temperature. It was observed that benzocaine suspensions formulated without the vinylpyrrolidone copolymer showed very high incidence of clogging (about 35%). On the other hand, formulations of benzocaine suspensions containing the vinylpyrrolidone copolymer did not show any malfunction. Over 300 aerosol cans representing about 15 various formula modifications were evacuated and no valve clogging was observed.

What is claimed is:

1. An anesthetic compositon comprising a therapeutically effective amount of powdered benzocaine suspended in an essentially anhydrous carrier and containing an effective amount of a vinylpyrrolidone and a long chain alpha-olefin copolymer of the formula:

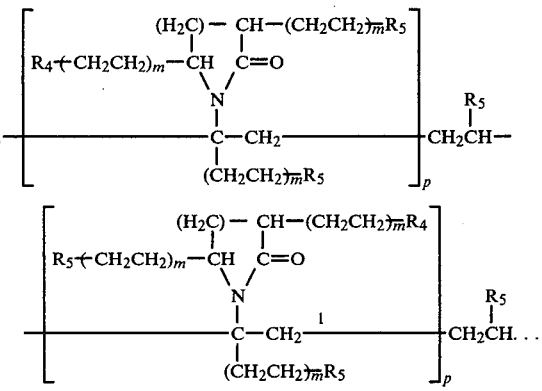

wherein $R_5$ is selected from the group consisting of hydrogen and alkyl, of from 1 to about 180 carbon atoms, p is an integer of from 10 to 100, and wherein the m's independently represent a numerical value of 0 to 1; when m is zero, $R_5$ is hydrogen; when m is 1, $R_5$ is selected from the group consisting of hydrogen and alkyl of from 1 to about 180 carbon atoms, and wherein at least one of the m's in at least one of the N-vinylpyrrolidone moieties has the value of 1;

the ratio of the said copolymer to benzocaine present is in the range of from about 0.05 parts to about 4 parts of copolymer to 1 part of benzocaine which is sufficient to significantly suppress crystal growth of said benzocaine on storage.

2. A composition according to claim 1 in which said carrier is a liquid carrier.

3. A composition according to claim 2 in which the ratio of the copolymer to benzocaine present is in the range of from about 0.2 parts to about 1part of copolymer to 1 part of benzocaine.

4. A composition according to claims 1, 2 or 3 in which the benzocaine is present in the range of from about 1% to about 30% by weight based on the total weight of the composition.

5. A composition according to claim 1, 2 or 3 in which the benzocaine is present in the range of from about 2% to about 20% by weight based on the total weight of the composition.

6. A composition according to claim 1 in the form of a foamable liquid.

7. A composition according to claim 1 in the form of an aerosol product.

8. A composition according to claim 1 in which said carrier is a solid.

9. A composition according to claim 8 in which the ratio of copolymer to benzocaine present is in the range from about 0.2 parts to about 1 part of copolymer to 1 part of benzocaine.

10. A composition according to claims 8 or 9 in which the benzocaine is present in the range of from about 1% to about 30% by weight based on the total weight of the composition.

11. A composition according to claims 8 or 9 in which the benzocaine is present in the range of from about 2% to about 20% by weight based on the total weight of the composition.

12. A composition according to claim 8 in the form of a suppository.

13. A composition according to claim 8 in the form of an ointment.

14. A composition according to claim 8 in the form of a gel.

15. A composition according to claim 8 in the form of an anhydrous cream.

16. A composition according to claim 1 in which said copolymer has a molecular weight in the range of from about 7,000 to 20,000.

17. A composition according to claim 16 in which said copolymer is PVP-Eicosene copolymer.

18. A composition according to claim 16 in which said copolymer is PVP-Hexadecene copolymer.

19. A composition according to claim 18 in which the ratio of said copolymer to benzocaine is in the range of from about 0.05 parts to about 4 parts of copolymer to 1 part of benzocaine.

* * * * *

UNITED STATES PATENT AND TRADEMARK OFFICE
CERTIFICATE OF CORRECTION

PATENT NO. : 4,241,048
DATED : December 23, 1980
INVENTOR(S) : Taras Durbak and Ara Nersesian It is certified that error appears in the above-identified patent and that said Letters Patent are hereby corrected as shown below:

Column 2, in the second line of the formula, change "$R_4$" to -- $R_5$ --.

Column 2, in the sixth line of the formula, change "$R_4$" to -- $R_5$ --.

Column 8, in the second line of the formula, change "$R_4$" to -- $R_5$ --.

Column 8, in the sixth line of the formula, change "$R_4$" to -- $R_5$ --.

Signed and Sealed this

Ninth Day of June 1981

[SEAL]

Attest:

RENE D. TEGTMEYER

*Attesting Officer*     *Acting Commissioner of Patents and Trademarks*